United States Patent
Morita et al.

(10) Patent No.: US 6,740,759 B1
(45) Date of Patent: May 25, 2004

(54) METHOD FOR PRODUCING 2-ALKYL-4-ISOTHIAZOLINE-3-ONE

(75) Inventors: Masayuki Morita, Tokyo (JP); Guo-bin Liu, Tokyo (JP); Noriko Yoneta, Tokyo (JP)

(73) Assignee: Chemicrea, Inc., Tokyo (JP)

( * ) Notice: Subject to any disclaimer, the term of this patent is extended or adjusted under 35 U.S.C. 154(b) by 0 days.

(21) Appl. No.: 09/666,481

(22) Filed: Sep. 20, 2000

(30) Foreign Application Priority Data

Dec. 27, 1999 (JP) .......................... 11/369205

(51) Int. Cl.$^7$ ............................ C07D 275/03
(52) U.S. Cl. ...................................... 548/213
(58) Field of Search ........................ 548/213

(56) References Cited

U.S. PATENT DOCUMENTS

| | | |
|---|---|---|
| 3,849,430 A | 11/1974 | Lewis et al. |
| 4,939,266 A | 7/1990 | Bayer et al. |
| 5,068,338 A | 11/1991 | Bayer et al. |
| 5,068,344 A | 11/1991 | Petigara et al. |
| 5,090,428 A | 2/1992 | Greene et al. |
| 5,312,827 A | 5/1994 | Bayer et al. |
| 5,420,290 A | 5/1995 | Bayer et al. |
| 5,453,507 A | 9/1995 | Hahn et al. |
| 5,466,818 A | 11/1995 | Petigara |

FOREIGN PATENT DOCUMENTS

GB         2308364 A  *  6/1997

OTHER PUBLICATIONS

Burri, "Tilcotil Studies, (3+2) Additions with Isothiazol–3(2H)–one 1, 1–Dioxide", 1989, pp. 1416–1427, Helvetica Chimica Acta—vol. 72.

European Search Report, Dated Apr. 2, 2001, 3 pages.

* cited by examiner

*Primary Examiner*—Laura L. Stockton
(74) *Attorney, Agent, or Firm*—Nixon Peabody LLP; Donald R. Studebaker

(57) ABSTRACT

Chlorinating agent is reacted with a compound represented by formula (I)

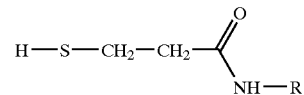

(wherein R represents C1 to C8 alkyl groups or aralkyl groups) or a compound represented by formula (II)

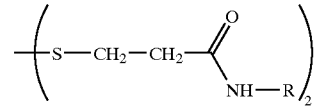

in a solvent in which hydrogen chloride is insoluble or has low solubility.

6 Claims, No Drawings

METHOD FOR PRODUCING 2-ALKYL-4-ISOTHIAZOLINE-3-ONE

BACKGROUND OF THE INVENTION

1. Field of the invention

The present invention concerns a method of producing 2-alkyl-4-isothiazoline-3-one which is useful as an industrial disinfectant

2. Description of the Prior Art

The isothiazoline-3-one which has been used as industrial disinfectants has been a mixture of 2-alkyl-4-isothiazoline-3-one and 5-chloro-2-alkyl-4-isothiazoline-3-one. However, with the recent emergence of problems of mutagenicity associated with 5-chloro-2-alkyl-4-isothiazoline-3-one, the demand has risen for 2-alkyl-4-isothiazoline-3-one with a low or no content of 5-chloro-2-alkyl-4-isothiazoline-3-one.

Numerous methods of producing 2-alkyl-4-isothiazoline-3-ones have been disclosed. For example, as presented in U.S. Pat. No. 3,849,430 and European Patent 95907, N-alkyl-3-mercaptopropionamide is chlorinated in ethyl acetate solvent to obtain a mixture of 2-alkyl-4-isothiazoline-3-one and 5-chloro-2-alkyl-4-isothiazoline-3-one. However, the methods of production stated here provide no means of reducing the content of 5-chloro-2-alkyl-4-isothiazoline-3-one.

The method presented in European Patent 0437354 states a method of separating 2-alkyl-4-isothiazoline-3-one at comparatively high purity by neutralizing only the 5-chloro-2-alkyl-4-isothiazoline-3-one in a mixture of 2-alkyl-4-isothiazoline-3-one hydrochloride and 5-chloro-2-alkyl-4-isothiazoline-3-one hydrochloride using anhydrous ammonia. However, the procedures in this production method are complex and the level of 5-chloro-2-alkyl-4-isothiazoline-3-one which brings about mutagenicity is present as before. Furthermore, a significant amount of 2-alkyl-4-isothiazoline-3-one is lost when attempting to remove 5-chloro-2-alkyl-4-isothiazoline-3-one.

Furthermore, European patent 0678510 presents a method in which a mixture of 2-alkyl-4-isothiazoline-3-one hydrochloride and 5-chloro-2-alkyl-4-isothiazoline-3-one hydrochloride is heated in organic solvent. 2-alkyl-4-isothiazoline-3-one hydrochloride is refined utilizing the difference in solubility between 2-alkyl-4-isothiazoline-3-one hydrochloride and 5-chloro-2-alkyl-4-isothiazoline-3-one hydrochloride in organic solvent, but a level of 5-chloro-2-alkyl-4-isothiazoline-3-one sufficient to bring about mutagenicity remains as before, and the loss of 2-alkyl-4-isothiazoline-3-one remains unavoidable.

As indicated above, all prior art is to obtain 2-alkyl-4-isothiazoline-3-one through purification of a mixture contaminated with 5-chloro-2-alkyl-4-isothiazoline-3-one rather than preferentially producing the desired 2-alkyl-4-isothiazoline-3-one.

However, the complete removal of 5-chloro-2-alkyl-4-isothiazoline-3-one through refining procedures remains difficult, and some of the 2-alkyl-4-isothiazoline-3-one is inevitably lost. Furthermore, the production procedures become more complex as the refining process is incorporated. Accordingly, in order to obtain 2-alkyl-4-isothiazoline-3-one of high purity in an industrially profitable manner, it is advantageous to suppress the formation of 5-chloro-2-alkyl-4-isothiazoline-3-one in the production stage as much as possible, and to minimize the loss of 2-alkyl-4-isothiazoline-3-one associated with purification.

SUMMARY OF THE INVENTION

In light of aforementioned circumstances, the purpose of the present invention is to provide a method of obtaining high-purity 2-alkyl-4-isothiazoline-3-one in a profitable yield through an industrially simple method, which does not contain 5-chloro-2-alkyl-4-isothiazoline-3-one or contains it at a level low enough so as not to bring about mutagenicity.

The inventors conducted thorough examinations into methods of producing 2-alkyl-4-isothiazoline-3-one in which the generation of 5-chloro-2-alkyl-4-isothiazoline-3-one is greatly reduced, the results of which revealed the unanticipated fact that the selectivity of 2-alkyl-4-isothiazoline-3-one and 5-chloro-2-alkyl-4-isothiazoline-3-one produced varies greatly with the type of solvent used in the reaction. Specifically, a correlation between the solubility of the hydrogen chloride in the solvent used in the reaction and the ratio of production of 2-alkyl-4-isothiazoline-3-one to 5-chloro-2-alkyl-4-isothiazoline-3-one was discovered that led to the completion of the present invention.

According to the present invention, the method of producing 2-alkyl-4-isothiazoline-3-one represented by general formula (III)

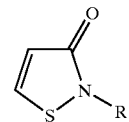

(wherein R represents C1 to C8 alkyl groups or aralkyl groups) is characterized by the fact that the compound represented by formula (I) a

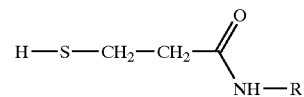

(wherein R has the same significance as in aforementioned formula (III)) or the compound represented by formula (II)

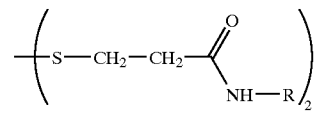

(wherein R has the same significance as in aforementioned formula (III)) are reacted in a solvent in which hydrogen chloride is insoluble or has low solubility with a chlorinating agent with a ratio of two equivalents of chlorinating agent per mol of formula (I) or three mole equivalents of chlorinating agent per mol of formula (II).

R in formula (I), (II) and (III) represents C1 to C8 alkyl groups or aralkyl groups. Methyl groups or normal octyl groups are preferred industrially.

Aforementioned solvent preferably should be inert to the compounds of formula (I), formula (II), formula (III) and the chlorinating agent. Inertness means that the solvent does not react with formula (I), formula (II), formula (III) or with chlorinating agent.

Furthermore, aforementioned solvent would be preferably those in which hydrogen chloride is insoluble or has low solubility. More specifically the solubility of hydrogen chloride in the preferred solvent at normal temperature/pressure would preferably be a molar fraction of 0.04 or less, more preferably 0.03 or less, still more preferably 0.02 or less.

Aforementioned solvents would preferably be selected from the organic solvents, especially from halogenated aliphatic hydrocarbons, halogenated aromatic hydrocarbons and aliphatic hydrocarbons. The solvent is preferably dichloromethane, dichloroethane, trichloroethane, tetrachloroethane, chloroform, carbon tetrachloride, monochlorobenzene, dichlorobenzene, pentane, hexane, cyclohexane, heptane, and octane.

In performing the present invention it is more preferable to isolate the hydrochloride of formula (II) which results from the reaction of the compounds of formula (I) or formula (II) with the chlorinating agent, and wash the salt with a solvent with which the salt does not react and in which the solubility of the salt is low.

Since the present invention of producing 2-alkyl-4-isothiazoline-3-one of the formula (III)

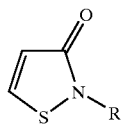

(wherein R represents C1 to C8 alkyl groups or aralkyl groups) is characterized by the fact that compound of the formula(I)

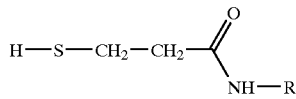

(wherein R has the same significance as in aforementioned formula (III)) or the compound represented by formula (II)

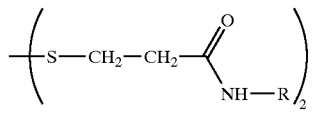

(wherein R has the same significance as in aforementioned formula (III)) is reacted in a solvent in which hydrogen chloride is insoluble or has low solubility with a chlorinating agent with a ratio of two mole equivalent per mole of compound of formula (I) or three mole equivalent per mole of compound of formula (II), virtually no 5-chloro-2-alkyl-4-isothiazoline-3-one, a mutagenic substance, is present and 2-alkyl-4-isothiazoline-3-one can be obtained at high selectivity.

Furthermore, since 2-alkyl-4-isothiazoline-3-one can be obtained selectively, purification need not be repeated as in the conventional method cited above, and leads to a quite economical process with minimal loss in yield from the refining step.

Aforementioned effects can be attained by using a solvent in which the solubility of hydrogen chloride is under 0.04 in molar fraction at normal temperature/pressure.

The production of by-products can be efficiently reduced by using a solvent in which formula (I), formula (II), formula (III) and chlorinating agent are inert.

Furthermore, higher-purity 2-alkyl-4-isothiazoline-3-one can be produced by removing the hydrochloride of formula (III) which is produced through reaction of the compound of formula (I) or formula (II) with chlorinating agent and then adding the process of washing the hydrochloride with a solvent in which this hydrochloride has low solubility and which does not react with the hydrochloride.

DESCRIPTION OF THE PREFERRED EMBODIMENTS

The preferred mode of implementation is explained in detail. Specifically, the method of producing 2-alkyl-4-isothiazoline-3-one represented by general formula (III)

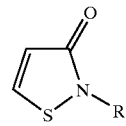

(wherein R represents C1 to C8 alkyl groups or aralkyl groups) is characterized by the fact that the compound represented by formula (I)

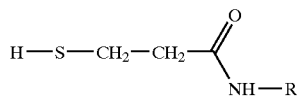

(wherein R has the same significance as in aforementioned formula (III)) or the compound represented by formula (II)

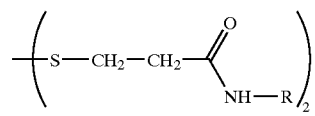

(wherein R has the same significance as in aforementioned formula (III)) are reacted in a solvent in which hydrogen chloride is insoluble or has low solubility with chlorinating agent.

There is no special limitation on the method of synthesis oft compound represented by formula (I) or formula (II) used in the present invention. For example, the compounds of the formula (I) and formula (II) can be easily obtained from the corresponding alkyl esters by amidation with alkyl or aralkylamines in an inert organic solvent or without using any solvent. The compound represented by formula (I) or formula (II) may be refined by recrystallization or distillation and then used in this reaction or the crude product can be used adequately in this reaction if the residual content of amines are reduced to the minimum.

There is no specific limitation on the chlorinating agent used in this reaction. For example, chlorine gas, sulfuryl chloride, etc., may be used, but chlorine gas would be most industrially desirable. Since 5-chloro-2-alkyl-4-isothiazoline-3-one is readily produced if an excess of chlorination agent is used, only two molar equivalents of chlorinating agent should be used per mole of the compound of formula (I) and three molar equivalents of chlorinating agent should be used per mole of the compound of formula (II). Specifically, as shown in formula (IV) and formula (V) below, 1.8 to 2.5 moles, preferably 1.9 to 2.2 moles, more preferably 2.0 to 2.1 moles should be used when using the compound of formula (I) while 2.8 to 3.5 moles, preferably 2.9 to 3.2 moles, more preferably 3.0 to 3.1 moles should be used when using the compound of formula (II).

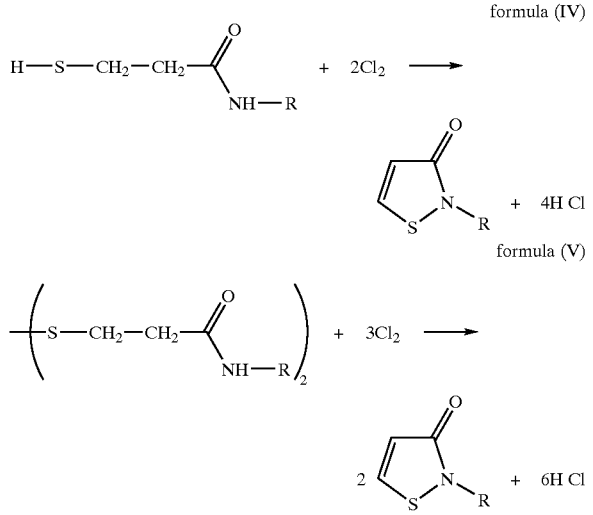

The solvent used in this invention should be the one in which hydrogen chloride is insoluble or has low solubility. The solubility of hydrogen chloride preferably should be under 0.04 as molar fraction. A smaller molar fraction value denotes lower solubility of hydrogen chloride in the solvent. The production of 5-chloro-2-alkyl-4-isothiazoline-3-one can be suppressed with the lower fraction value. Desirable solvents include halogenated aliphatic hydrocarbons, halogenated aromatic hydrocarbons and aliphatic hydrocarbons. Examples include dichloromethane (0.013 (1 atm, 298.15K, the same below)) dichloroethane (0.038), trichloroetharie (0.031), tetrachloroethane (0.025), chloroform (0.022), carbon tetrachloride (0.013), monochlorobenzene (0.0312), dichlorobenzene (0.022), pentane (0.005), cyclohexane (0.015), hexane (0.011), heptane (0.015), and octane (0.016). Dichloromethane, dichloroethane, trichloroethane, tetrachloroethane, chloroform, carbon tetrachloride, and monochlorobenzene would be more desirable. In addition, a mixed solvent comprising two or more solvents selected from aforementioned group may be used.

There is no specific limitation on the amount of solvent used, but 2 to 10 times the amount of compound of formula (I) or of formula (II) would be desirable, and 3 to 5 times the amount would be more desirable. The reaction may be carried out at any reaction temperature that is below the boiling point of the solvent in use. Hydrogen chloride gas is generated during the reaction, as shown in aforementioned formula (IV) and formula (V). Some of the hydrogen chloride gas that is generated forms a hydrochloride with isothiazoline-3-ones, some is dissolved in the solvent, and some is released from the reaction system. The hydrogen chloride in the solvent may be removed as required by heating, displacement with nitrogen gas, or under vacuum, etc.

As indicated above, the generation of 5-chloro-2-alkyl-4-isothiazoline-3-one can be suppressed by the present invention and 2-alkyl-4-isothiazoline-3-one can be selectively obtained, but the slight amount of 5-chloro-2-alkyl-4-isothiazoline-3-one present in the reaction mixture should be removed by the filtration of the hydrochloride of 2-alkyl-4-isothiazoline-3-one that is generated in the reaction, followed by washing the hydrochloride with any solvent in which it has low solubility and with which it does not react. The loss of 2-alkyl-4-isothiazoline-3-one is slight even if such purification processes is added.

The hydrochloride salt of 2-alkyl-4-isothiazoline-3-one can be converted to 2-alkyl-4-isothiazoline-3-one by dispersion in water, neutralization with base, extraction with inert organic solvent, and removal of the solvent. There is no specific limitation on the kinds of bases used in neutralization. Among these, inorganic bases such as sodium carbonate are preferable in terms of ease of handling and economy. There is no specific limitation on the temperature used in neutralization, but a temperature below 50° C. is preferable since it reduces coloration of the product.

The 2-alkyl-4-isothiazoline-3-one thus obtained in this manner has essentially no 5-chloro-2-alkyl-4-isothiazoline-3-one or a content of less than 0.5% and is a very pure product that does not bring about mutagenicity.

WORKING EXAMPLE 1

Both 120 g (0.508 mol) of N,N'-dimethyl-3,3'-dithiopropionamide and 480 ml of dichloromethane were charged in a two-liter four-necked flask equipped with a stirrer, a chlorine gas inlet tube, a thermometer and a condenser fitted with a calcium chloride condenser. 108 g (1.523 mol) of chlorine gas was introduced into the solution at a temperature range of 39–41° C. over a period of 3 hours and 15 minutes, followed by overnight stirring at room temperature. The precipitated crystals were filtered with suction, and were washed with dichloromethane. The crystals were dispersed in 400 ml of water and neutralized with sodium carbonate to pH7. The solution was extracted with dichloromethane, and the solvent was removed to give 90.12 g (77% yield) of 2-methyl-4-isothiazoline-3-one as pale brown solid.

WORKING EXAMPLE 2

A reaction was carried out under the same conditions as in working Example 1 except for the use of cyclohexane (molar fraction 0.015 1 atom 298.15K) as the solvent, as shown in Table 1, and 2-methyl-4-isothiazoline-3-one was obtained in 70% yield.

WORKING EXAMPLE 3

A reaction was carried out under the same conditions as in Working Example 1 except using chloroform as the reaction solvent and in washing the hydrochloride salt, and 2-methyl-4-isothiazoline-3-one was obtained in 75% yield.

WORKING EXAMPLE 4

A reaction was carried out under the same conditions as in Working Example 1 except for the use of N,N'-di-n-octyl-3,3-dithiopropionamide as the starting material, and using dichloromethane as the reaction solvent and using monochlorobenzene in washing the hydrochloride salt, and 2-n-octyl-4-isothiazoline-3-one was obtained in 71% yield.

WORKING EXAMPLE 5

A reaction was carried out under the same conditions as in Working Example 4 except for the use of monochlorobenzene as the solvent of the reaction, and 2-n-octyl-4-isothiazoline-3-one was obtained in 71% yield.

WORKING EXAMPLE 6

A reaction was carried out under the same conditions as in Working Example 4 except for the use of a mixture of monochlorobenzene and dichlorobenzene as the solvent of the reaction, and 2-n-octyl-4-isothiazoline-3-one was obtained in 70% yield.

WORKING EXAMPLE 7

A reaction was carried out under the same conditions as in Working Example I except for the use of N,N'-dibenzyl-3,3'-dithioprionamide as the starting material and monochlorobenzene as the solvent of the reaction and of washing the hydrochloride salt, and 2-benzyl-4-isothiazoline-3-one was obtained in 70% yield.

COMPARATIVE EXAMPLE

A reaction was carried out under the same conditions as in Working Example 1 except for the use of ethyl acetate as the solvent, and 2-methyl-4-isothiazoline-3-one was obtained in 51% yield.

TABLE 1

| | R | Solvent used in reaction | Solvent used in washing hydrochloride salt |
|---|---|---|---|
| working example 1 | Methyl group | Dichloromethane (0.013) | Dichloromethane |
| Working example 2 | Methyl group | Cyclohexane (0.015) | Dichloromethane |
| Working example 3 | Methyl group | Chloroform (0.022) | Chloroform |
| Working example 4 | Normal octyl group | Dichloromethane (0.013) | Monochlorobenzene |
| working example 5 | Normal octyl group | Monochlorobenzene (0.0312) | Monochlorobenzene |
| Working example 6 | Normal octyl group | Mixed solvent of monochloro-benzene & dichloromethane (0.025) | Monochlorobenzene |
| Working example 7 | Benzyl gtoup | Monochlorobenzene (0.0312) | Monochlorobenzene |
| Comparative example | Methyl group | Ethyl acetate (0.240) | Etyl acetate |

The numbers in the table enclosed by parentheses in the column of solvents used in the reaction denote the molar fraction of the solubility of hydrogen chloride at normal temperature/pressure. The purity of the crystals obtained in Working Examples 1 to 7 and in the Comparative Example was analyzed by high-performance liquid chromatography and submitted to mutagenicity (Ames) testing. Table 2 presents the results. A "+" signifies a positive adverse effect on the body while a "−" denotes no adverse effect.

TABLE 2

| | 2-alkyl-4-isothiazoline-3-one (%) | 5-chloro-2-alkyl-4-isothiazoline-3-one (%) | Ames test |
|---|---|---|---|
| Working Example 1 | >99.9 | <0.1 | − |
| Working Example 2 | >99.5 | <0.5 | − |
| Working Example 3 | >99.0 | <1.0 | − |
| Working Example 4 | >99.9 | <0.1 | − |
| Working Example 5 | >99.9 | <0.1 | − |
| Working Example 6 | >99.9 | <0.1 | − |
| Working Example 7 | >99.9 | <0.1 | − |
| Comparative Example | 47 | 53 | + |

As Table 2 indicates, the method of producing 2-alkyl-4-isothiazoline-3-one pursuant to the present invention yields 2-alkyl-4-isothiazoline-3-one with very high selectivity and with virtually no content of the mutagenic substance, 5-chloro-2-alkyl-4-isothiazoline-3-one. Furthermore, the results of Ames tests were negative in all working examples.

In the working examples the hydrochloride salt of 2-alkyl-4-isothiazoline-3-one was filtered and washed with a solvent, but as the reaction proceeds with high selectivity, 2-alkyl-4-isothiazoline-3-one of sufficient purity can be obtained without washing the hydrochloride salt.

In addition, all of the contents of Japanese Patent Application No. 11(1999)-369205 are incorporated into this specification by reference.

What is claimed is:

1. A method of producing 2-alkyl-4isothiazoline-3-one represented by the general formula (III),

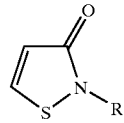

wherein the compound represented by formula (II),

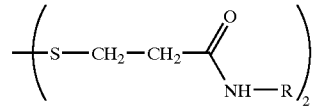

is reacted with chlorine as a chlorinating agent in dichloromethane as a solvent, in which hydrogen chloride is insoluble or exhibits low solubility, at a temperature of 39–41° C., according the reaction formula represented by:

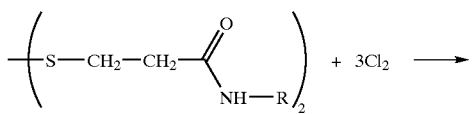

wherein R in the compounds of formulae (II) and (III) represents a C1 to C8 alkyl group or an aralkyl group, and wherein the amount of a 5-chloro-2-alkyl-4-isothiazoline-3-one contained in the 2-alkyl-4-isothiazoline-3-one produced is less than 0.1%.

2. The method producing a 2-alkyl4isothiazoline-3-one as defined in claim 1, wherein the R represents a methyl group.

3. The method producing a 2-alkyl-4-isothiazoline-3-one as defined in claim 1, wherein the R represents a normal octyl group.

4. The method producing a 2-alkyl-4-isothiazoline-3-one as defined in claim 1, further comprising the steps of filtrating a hydrochloride salt of the compound of formula (III) obtained from the reaction of the compound of formula II with chlorine, and washing the hydrochloride salt with a solvent which is inert to the hydrochloride salt and in which the hydrochloride salt exhibits low solubility.

5. The method producing a 2-alkyl-4-isothiazoline-3-one as defined in claim 2, further comprising the steps of filtrating a hydrochloride salt of the compound of formula (III) obtained from the reaction of the compound of formula II with chlorine, and washing the hydrochloride salt with a solvent which is inert to the hydrochloride salt and in which the hydrochloride salt exhibits low solubility.

6. The method producing a 2-alkyl-4-isothiazoline-3-one as defined in claim 3, further comprising the steps of filtrating a hydrochloride salt of the compound of formula (III) obtained from the reaction of the compound of formula II with chlorine, and washing the hydrochloride salt with a solvent which is inert to the hydrochloride salt and in which the hydrochloride salt exhibits low solubility.

* * * * *